(12) United States Patent
Clayman

(10) Patent No.: US 8,195,279 B2
(45) Date of Patent: *Jun. 5, 2012

(54) PORTABLE ELECTROCARDIOGRAM

(76) Inventor: Henry M. Clayman, Santa Fe, NM (US)

( * ) Notice: Subject to any disclaimer, the term of this patent is extended or adjusted under 35 U.S.C. 154(b) by 436 days.

This patent is subject to a terminal disclaimer.

(21) Appl. No.: 12/404,032

(22) Filed: Mar. 13, 2009

(65) Prior Publication Data
US 2010/0130845 A1 May 27, 2010

Related U.S. Application Data

(63) Continuation-in-part of application No. 11/925,545, filed on Oct. 26, 2007, now Pat. No. 7,751,872.

(51) Int. Cl.
*A61B 5/0404* (2006.01)
(52) U.S. Cl. .................. 600/509; 600/379; 600/382
(58) Field of Classification Search .................. None
See application file for complete search history.

(56) References Cited

U.S. PATENT DOCUMENTS

| | | | |
|---|---|---|---|
| 4,535,783 A * | 8/1985 | Marangoni | 600/524 |
| 4,606,352 A * | 8/1986 | Geddes et al. | 600/515 |
| 5,213,108 A * | 5/1993 | Bredesen et al. | 600/528 |
| 6,363,274 B1 * | 3/2002 | Scalisi et al. | 600/523 |
| 7,065,396 B2 * | 6/2006 | Hampton | 600/509 |
| 7,647,093 B2 * | 1/2010 | Bojovic et al. | 600/509 |
| 7,751,872 B2 * | 7/2010 | Clayman | 600/509 |
| 2002/0082491 A1 * | 6/2002 | Nissila | 600/391 |
| 2003/0045787 A1 * | 3/2003 | Schulze et al. | 600/382 |
| 2008/0027340 A1 * | 1/2008 | Kuo et al. | 600/509 |

\* cited by examiner

*Primary Examiner* — Kennedy Schaetzle
(74) *Attorney, Agent, or Firm* — Michael J. Buchenhorner

(57) ABSTRACT

An apparatus for measuring cardiac electric activity of a patient includes a tubular structure embodied in a lightweight, gently u-shaped form factor. The tubular structure includes: a center portion, a left handle in an upright end of the tubular structure, a right handle in a contralateral upright end; a connector positioned in the center portion; first and second receiving electrodes in the right and left handles; and an efferent cable for coupling the connector with a processor for electronically inverting signals obtained from the electrodes to produce vectors enabling a calculation of a conventional twelve-lead electrocardiogram. The processor is operatively coupled with a fourth electrode affixed to the patient's ear.

22 Claims, 11 Drawing Sheets

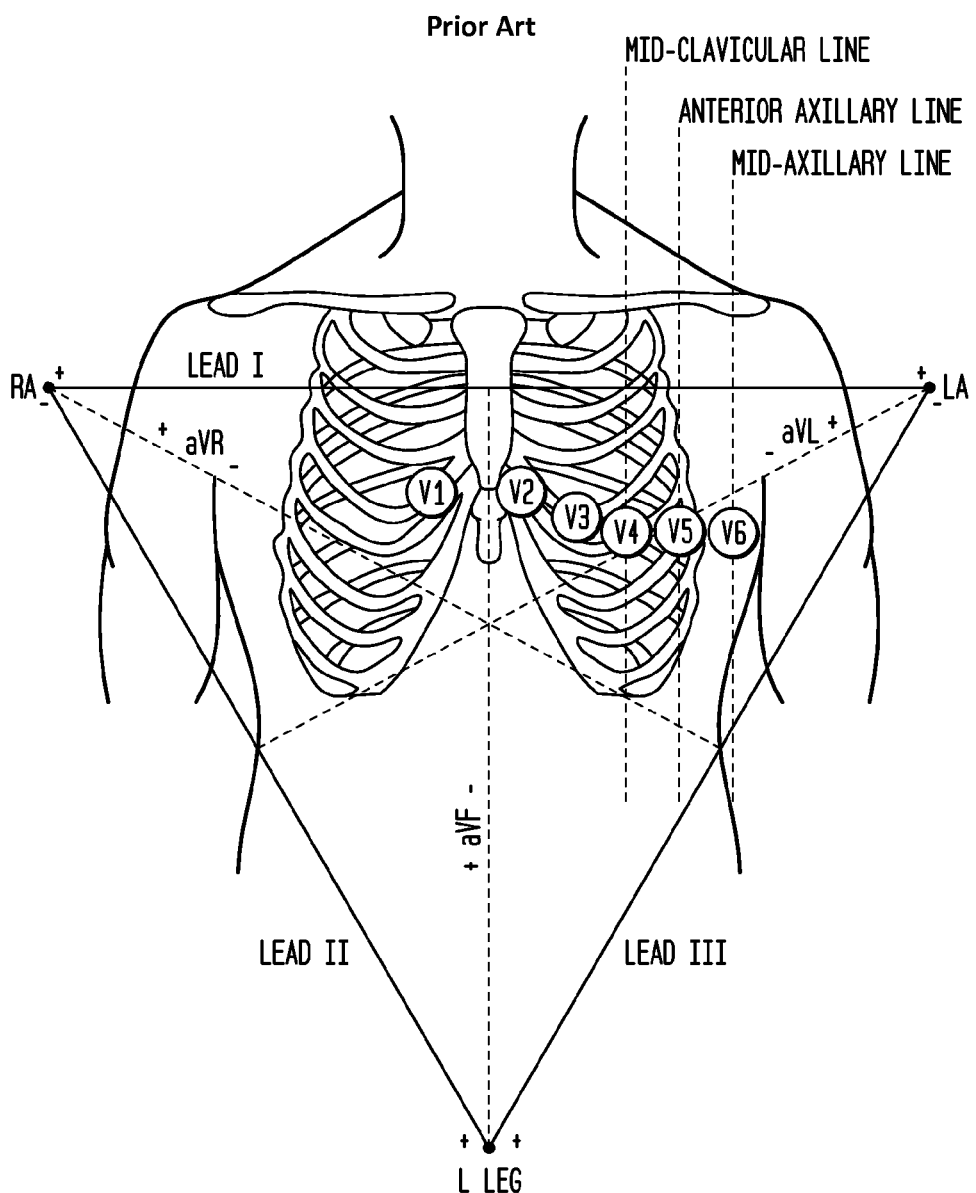

PORTABLE ELECTROCARDIOGRAM

CROSS-REFERENCE TO RELATED APPLICATIONS

This application is a continuation-in-part of, and claims priority from, commonly-owned, U.S. patent application Ser. No. 11/925,545 filed on Oct. 26, 2007, now U.S. Pat. No. 7,751,872, which is incorporated by reference as if fully set forth herein.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of equipment for monitoring the electrical activity of the heart, and particularly to a three or four-lead method for monitoring cardiac electrical activity.

BACKGROUND OF THE INVENTION

An electrocardiogram is a test that graphically records the electrical activity of the heart. The electrocardiogram or ECG (sometimes called EKG) is used worldwide as a relatively simple way of diagnosing many heart conditions. It records the small electric waves being generated during heart activity using body surface electrodes attached to a patient. The electrodes are placed in a particular pattern for clinical use because electrical signals generated by a human heart appear in a characteristic pattern throughout the body, and on its surface subject to their position.

A procedure developed by Willem Einthoven in 1901 inter-related three electrodes specifically oriented on the body (right arm, left arm, and left leg). These electrodes are at the apices of a physiological triangle known as Einthoven's triangle, as shown in FIG. 1a. The difference in electrical potential between the left and right arms is designated lead I; lead II is the difference in electrical potential between the left leg and right arm; and lead III is the difference in electrical potential between the left leg and left arm. Thus, the Einthoven triangle resembles a triangle standing on its tip "▼."

These electrodes provide bipolar recordings of the voltage differential between two electrodes. By convention, the positive electrode is placed on the left arm, with the negative electrode on the right arm. In the lead II configuration, the positive electrode is on the left leg and the negative electrode is on the right arm. Lead III has the positive electrode on the left leg and the negative electrode on the left arm. The limb leads can be attached to the end of the limb (wrists and ankles) or at the origin of the limb (shoulder or upper thigh). The difference in electrical potential between two of the electrodes constitutes the signal.

Referring to FIG. 1b there is shown a simplified illustration of a conventional electrocardiograph 100 in place on a patient. The ECG 100 requires at least three leads (therefore three electrodes are needed). These three electrodes are applied one on each of the patient's arms 110 and 112. The third electrode 120 is applied on the patient's left leg.

A fourth electrode 140 is placed on the patient's right leg as an electrical ground. The ground can be at other locations on the body but at a reasonable distance from the other electrodes to ensure a good signal. In addition, there are six precordial (chest) leads 160 designated $V_1$-$V_6$ (not shown here), for a total of twelve leads. Their conventional placement is illustrated in FIG. 1c.

The electrodes are easy to apply and this conventional placement of electrodes works well in a hospital setting and in a doctor's office. The problem arises, however, when it is desirable and sometimes necessary for an ECG to be used outside of a conventional medical setting. For example, a patient with chronic heart problems may want to have a portable ECG in the home or the office. Airlines may find it necessary to have a portable ECG in airplanes for in-flight emergency use. The signals produced by a portable unit can be transmitted to a doctor on the ground who can then interpret the signals and advise the airline staff as to whether to use an on-board defibrillator.

Electrodes must be positioned in an anatomically correct pattern so that the readings are valid. One problem with this conventional electrode placement is that leg electrodes are not conducive to portability.

SUMMARY OF THE INVENTION

Briefly, according to an embodiment of the present invention, a method for measuring cardiac electrical activity of a patient includes: attaching a first electrocardiogram electrode to a patient's ear; attaching second and third electrodes to both hands of the patient, forming an inverted Einthoven triangle of electrocardiograph electrodes on the patient. A fifth electrode is attached to the patient's chest area. An electrical ground electrode is then attached to the patient's contralateral ear. The electrodes are coupled to a connector by lead wires and the connector is operatively coupled to a processor. The method further electronically inverts signals obtained from the electrodes to produce a conventional electrocardiogram recording using the processor.

According to another embodiment of the present invention, an apparatus for measuring cardiac electric activity of a patient includes a tubular structure embodied in a lightweight, gently u-shaped form factor. The tubular structure includes: a center portion, a left handle in an upright end of the tubular structure, a right handle in a contralateral upright end; a connector positioned in the center portion; first and second receiving electrodes in the right and left handles; and an efferent cable for coupling the connector with a processor for electronically inverting signals obtained from the electrodes to produce vectors enabling a calculation of a conventional twelve-lead electrocardiogram. The processor is operatively coupled with a fourth electrode affixed to the patient's ear.

According to another embodiment of the present invention, the apparatus is operable to transmit cardiac signals wirelessly and includes a circuit module for converting the signals from the lead wires.

BRIEF DESCRIPTION OF THE DRAWINGS

To describe the foregoing and other exemplary purposes, aspects, and advantages, we use the following detailed description of an exemplary embodiment of the invention with reference to the drawings, in which:

FIG. 1c shows the placement of leads $V_1$-$V_6$, according to the known art;

Figure 1A:
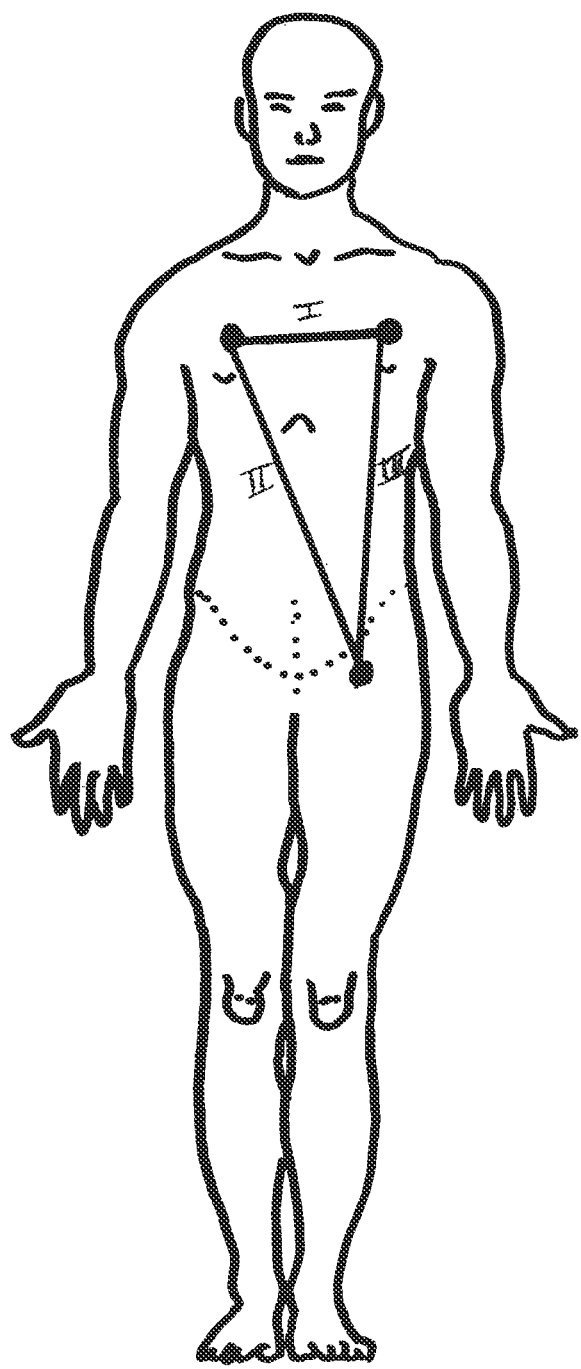
FIG. 1a shows an illustration of Einthoven's inverted triangle, according to the known art.
Figure 1B:
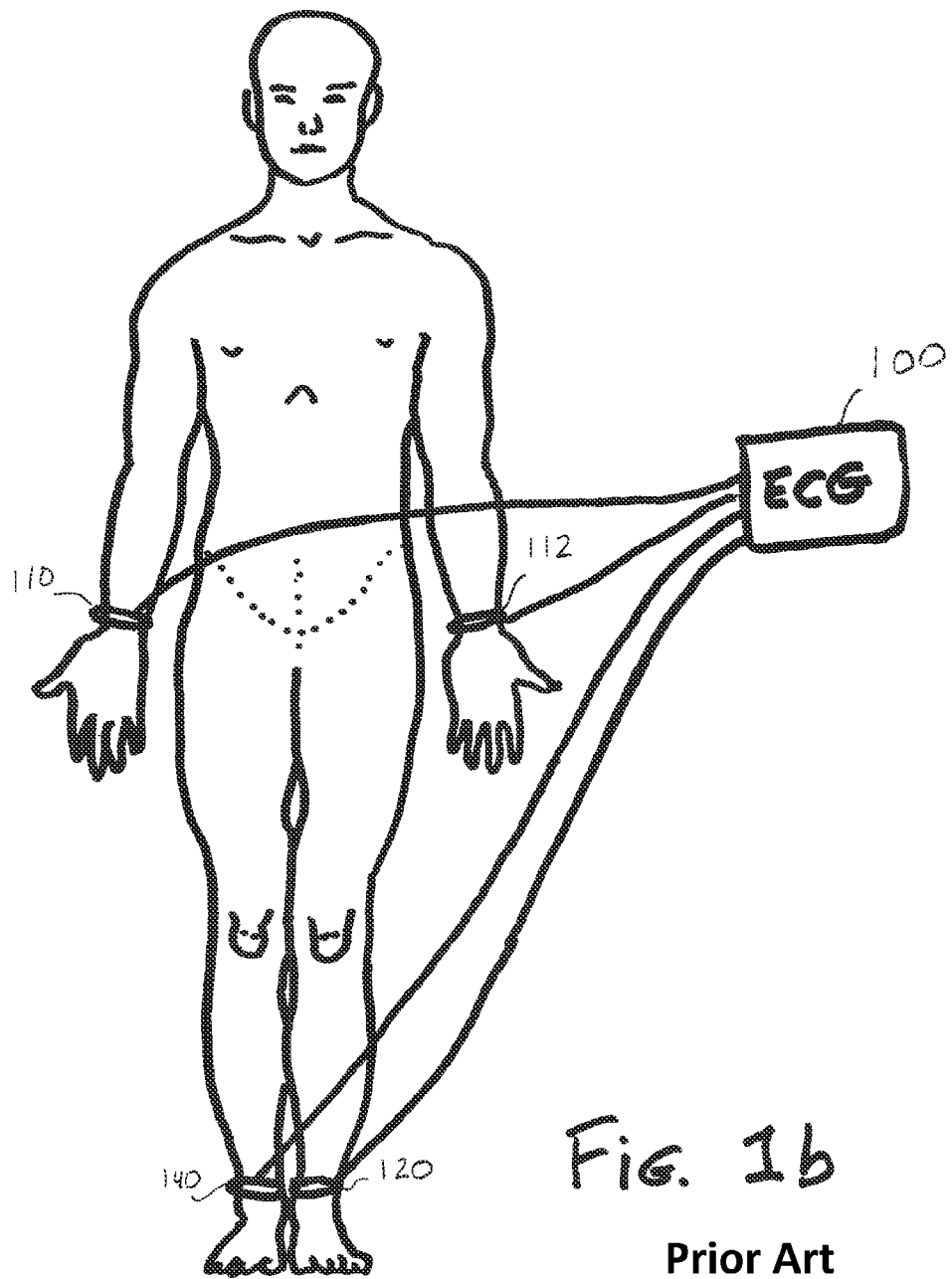
FIG. 1b shows an illustration of an electrocardiograph system according to the known art.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

I describe a method for recording the electrical activity of the heart using an inverted Einthoven triangle of electrodes. The current 12 lead ECG used in modern medicine is based upon placement of electrodes on anatomical markers and calculating the 12 ECG recordings derived from these positions. However, with the advancement of computer technology it is feasible to use fewer electrode positions to synthesize the customary 12 lead ECG. This is achieved by a computer algorithm which takes readings from the available leads and calculates the readings for the missing leads.

Figure 2:
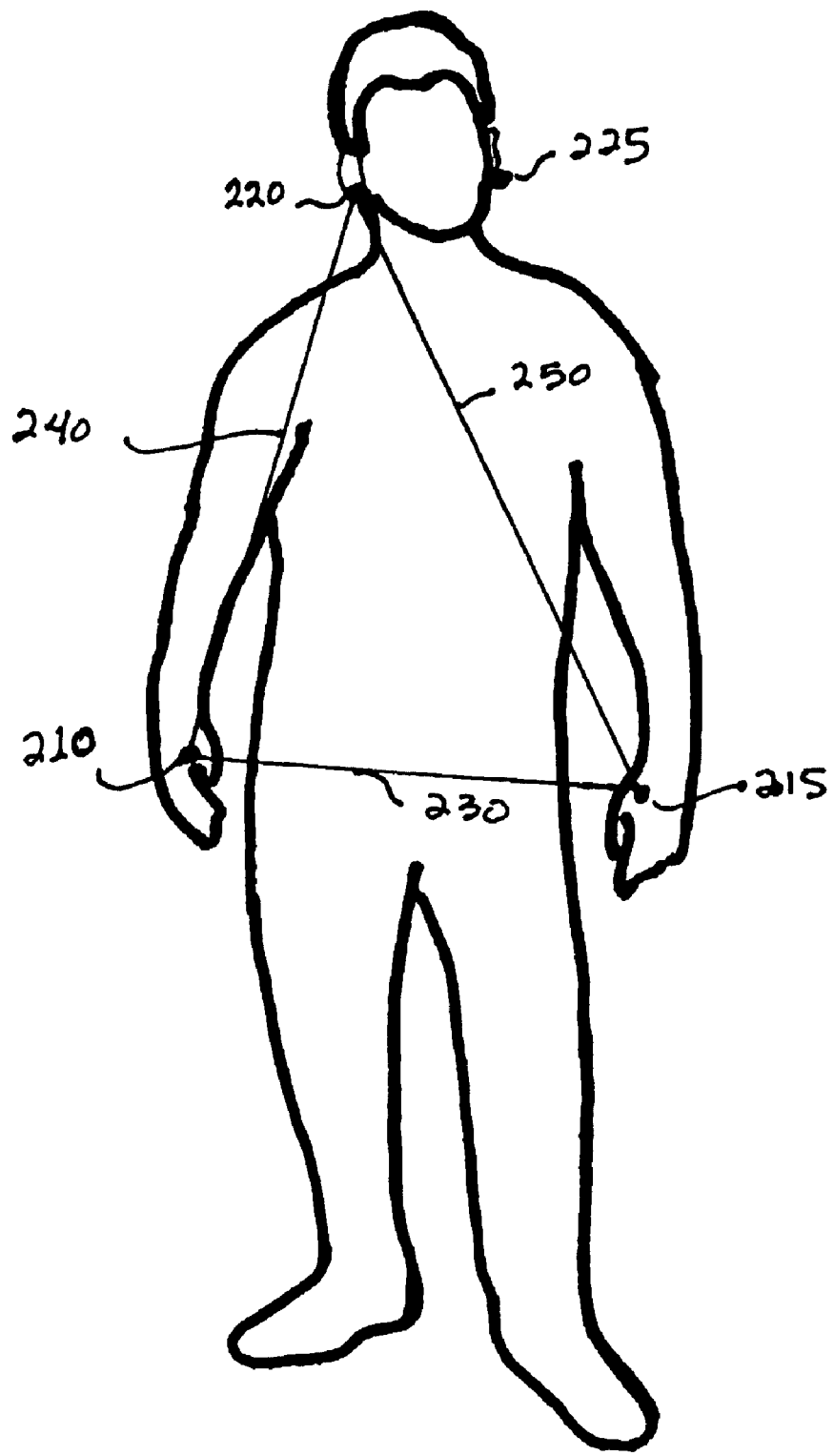
FIG. 2 shows an illustration of the placement of electrodes to form an inverted Einthoven triangle, according to an embodiment of the present invention.

Referring to FIG. 2 there is shown an exemplary placement of electrodes according to an embodiment of the present invention. In this example, receiving electrodes on the (R) 210 and (L) 215 hand and one receiving electrode on the (R) EAR 220 act as an inverted Einthoven triangle. The R 210 and L 215 hand electrodes produce lead I 230. The R ear 220 and L hand 215 electrodes produces lead II 240 and the R ear 220 and R hand 210 electrodes produce lead III 250. One electrode 225 is placed on the patient's left ear, to act as ground.

The above electrodes make contact with the patient's skin and pick up trans-cutaneous electrical signals from the patient's heart. Thus, electrical potential differences between the right arm, left arm, and ear can be measured. The ear electrode 220 forms the apex of the inverted Einthoven triangle, with the hand electrodes 210 and 215 forming the base of the triangle. Another electrode 225 used for ground potential may optionally be placed in the patient's contralateral ear as shown in FIG. 2.

The ear electrodes 220 and 225 may be embodied in an earphone form factor, or they may simply be clipped to the earlobes. The electrodes can be rectangular or some other shape. They may be suction, button, or plate electrodes. Each electrode has a substantially flat surface for secure attachment to a patient's skin. Modern electrodes are self-adhesive; but to aid in electrical conduction, a conductive gel is sometimes applied to the flat surface of each electrode before attachment. If necessary, tape can be used to secure the electrode. The non-contact surface of the electrode is a conductor attached to an electrode lead wire which in turn may be attached to a multiplex cable. The cable is preferably coupled with a connector. The connector includes ports for coupling with a reader and other input/output devices.

With electrode placement on the right arm, left arm, and right ear, the combination of left arm-right arm is equivalent to a standard lead I 230 ECG configuration. The right arm-right ear combination acts as an inverted lead II 240 and the left arm-right ear combination produces an inverted lead III 250. Readings from these two latter leads are transformed back to the conventional Einthoven configuration mathematically by taking into account: 1) the angular variation of the cardiac dipole measured by a right ear electrode as opposed to a left leg electrode; and 2) the magnitude variation of the cardiac dipole measured by a right ear electrode as opposed to a left leg electrode.

An electronic circuit, as used in conventional ECG devices, additionally inverts the electrical signals received from the electrodes to produce a conventional cardiac signal, which can be displayed on a monitor or transmitted to a remote location by landline or wireless means.

To facilitate use by non-medical personnel, standardized color coding of the electrodes and/or lead wires can be used, and the color codes can be made available to the patient.

In one embodiment, without precordial recordings, the minimum number of electrodes that can be advantageously used for cardiac monitoring is four: one receiving electrode in the patient's ear 220, two electrodes on each hand 210 and 215, and one electrode to be used as ground. This ground electrode 225 may be placed in the patient's contralateral ear.

The apex of the inverted Einthoven triangle is formed by a receiving electrode preferably located in or on the patient's ear. The system as described can be self-applied by a patient and is devoid of leg electrodes.

Figure 3:
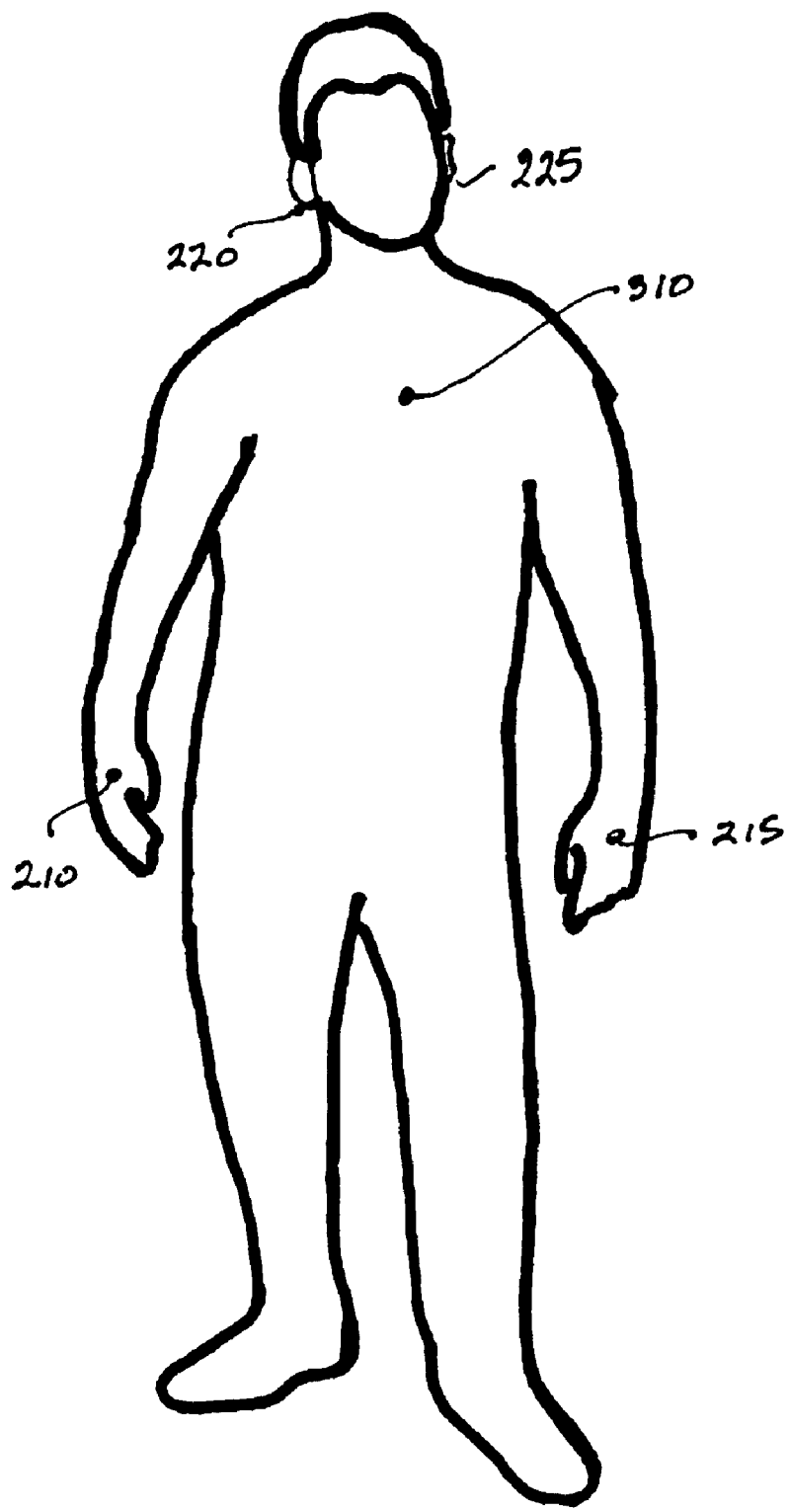
FIG. 3 shows an illustration with the chest electrode displaced to the left, according to an embodiment of the present invention.
Figure 4:
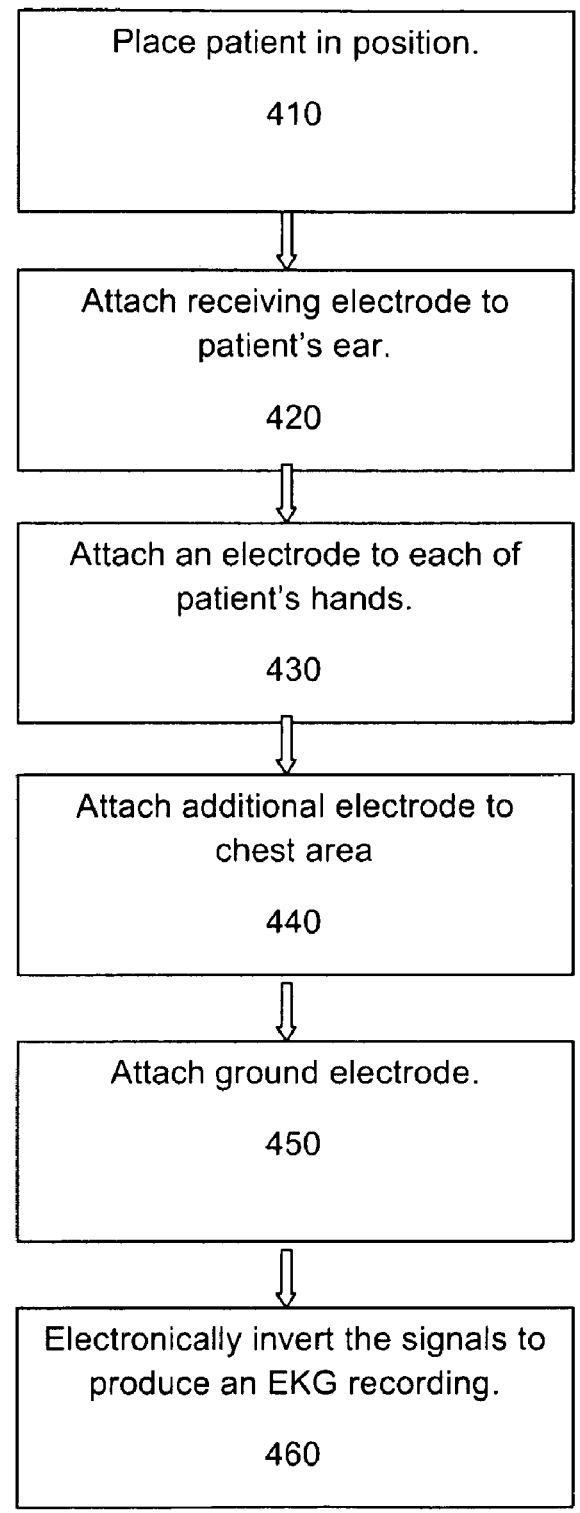
FIG. 4 is a flow chart of a method according to an embodiment of the present invention.

Up to this point, the embodiment presented herein has been described in commonly-owned, co-pending application Ser. No. 11/925,545. Now is presented a novel embodiment enabling the calculation of a 12-lead ECG. Referring to FIG. 3, there is shown an embodiment which differs from the previously described embodiment by the addition of a fifth electrode. The contact of a fifth electrode 310 in the chest area plus the other electrodes described above provide information which is input into the algorithm to produce vectors enabling the calculation of the customary 12 lead ECG.

Referring now to FIG. 3, there is shown an illustration depicting another embodiment of the present invention, wherein the chest electrode 310 is displaced to the left of the sternum (breast bone) taking into consideration that a person's cardiac silhouette is predominantly in the left side of the chest.

Figure 5A:
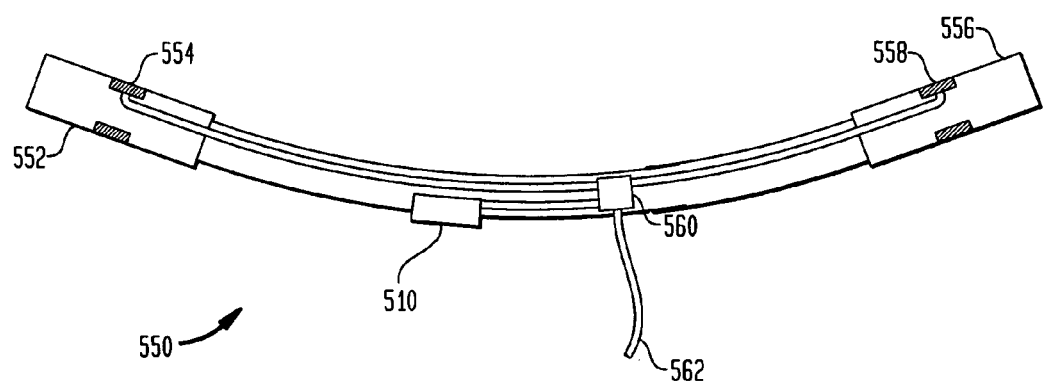
FIG. 5A shows a simplified illustration of a handlebar electrode, according to an embodiment of the present invention.

Referring now to FIG. 5A there is shown an embodiment wherein a "handlebar" is used to receive the cardiac signals. As shown in FIG. 5, a chest electrode 510 is disposed on the handlebar 550. This chest electrode 510 is able to "slide" along the center portion of the "handlebar" 550 a few inches in each direction to give some versatility to the chest and hand positions. A patient grasps the upright ends 552 and 556 of the handlebar 550. The handlebar 550 is aligned over the patient along the plane of the nipples. The center chest electrode 510 is positioned slightly to the left of the sternum. The patient grasps the ends of the handlebar 550 and places the handlebar 550 on his/her chest, making contact with the skin at the point of the chest electrode 510. When properly positioned, the ends of the handlebar 550 flare up and away from the patient, thus avoiding any contact with the patient's skin.

Figure 8:
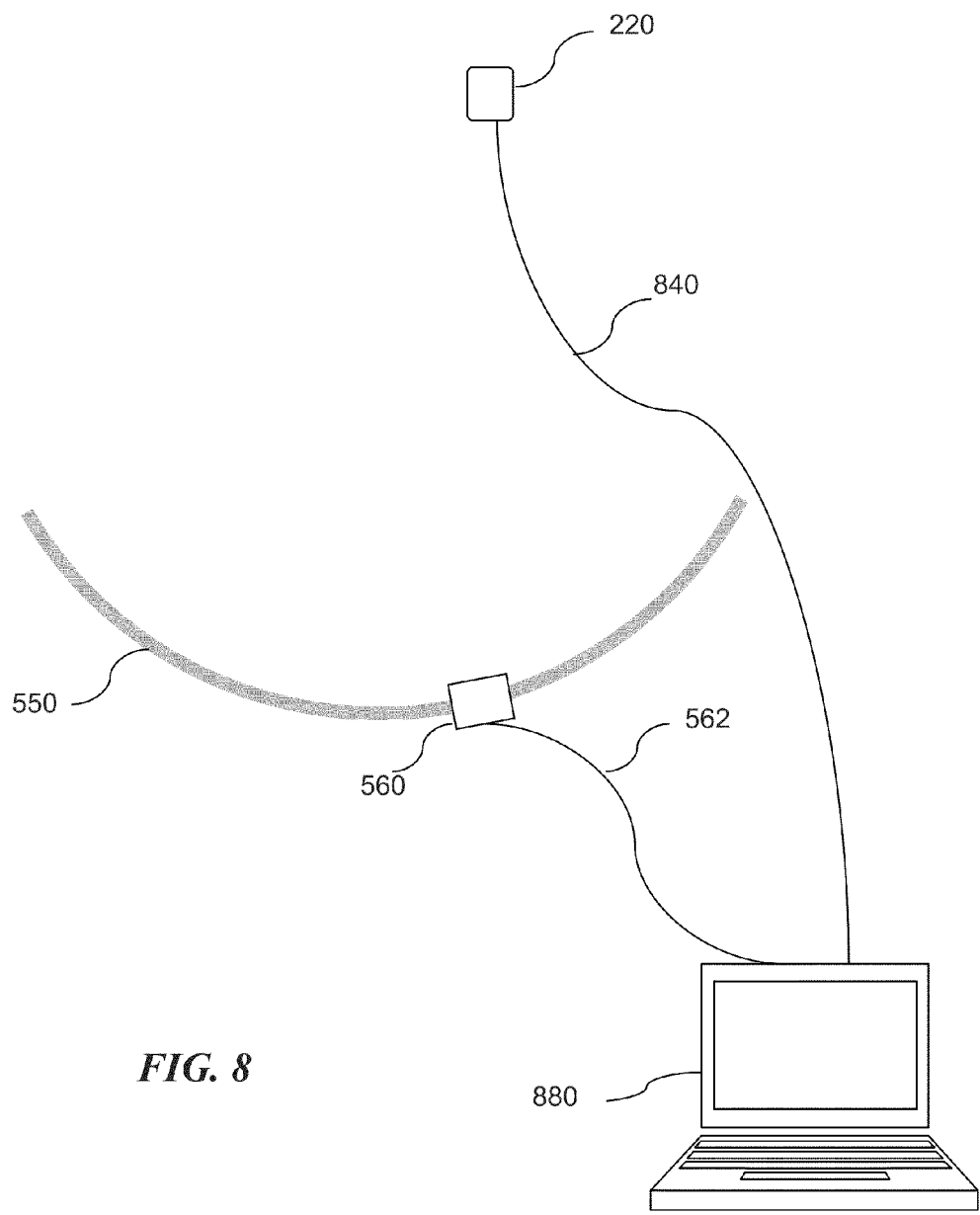
FIG. 8 shows the connector of the handlebar of FIG. 7 electrically coupled with an ear electrode, according to an embodiment of the present invention.

To secure accurate readings, a fourth electrode 220 (not shown here) is affixed to the patient's ear, forming the apex of the inverted Einthoven triangle. Lead wires from the fourth electrode 220 feed into a computer. As shown in FIG. 8, in an alternate embodiment, the lead wires 840 from the fourth electrode 220 are fed into the connector 560.

In another embodiment, the electrodes on the extremities of the handlebar 550 can also be fitted over the handlebar 550. In this embodiment, the electrodes are hollow cylindrical bars that fit over the upright ends of the handlebar 550.

The handlebar 550 can be formed of a thermoplastic, self-insulating material. Preferably, it should be amenable to molding. Alternately, a metal could also be used. In such an embodiment the internal wires would need to be covered by insulating sheaths and the hand electrodes would also need to be insulated.

The circumference of the handlebar 550 is preferably approximately four inches. The length of the handlebar 550 can be anywhere from 20-26 inches. The handlebar 550 form factor shown here embodies a gentle u-shape in order to avoid contact with the chest at any point other than the chest electrode 510. The gentle u-shape is shown here for exemplary purposes, not for limitation. It will be appreciated that other shapes may be advantageously used, such as, for example, a wide v-shaped form factor with the chest electrode at the apex of the "V."

In one embodiment, the right 556 and left 552 ends of the handlebar 550 are fixed contact surfaces which function as electrodes 554 and 558 and encircle the handlebar 550. The handles 552 and 556 are circumferential. This is similar to the grasp bars found on treadmills and exercise bikes which record a person's heart rate.

The electrodes 554 and 558 make contact with the patient's hands and are connected by internal wires to a connector 560 near the center of the handlebar 550 which is connected via an efferent cable 562 to a computer (not shown).

Figure 5B:
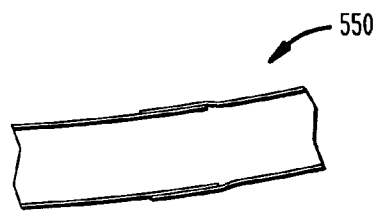
FIG. 5B shows two separate segments of the handlebar, according to an embodiment of the present invention.

Referring to FIG. 5B, in an alternate embodiment, the handlebar 550 can be formed in two separate pieces, making it easier for storage (as on a plane). FIG. 5B shows one embodiment wherein the two separate sections of the handlebar 550 fit together with an end piece of one section fitting into the slightly wider end piece of the other section, similar to the extension tubes of a vacuum cleaner hose. This allows the handlebar 550 to be assembled by hand or disassembled for easy storage when the handlebar 550 is not in use. Since the left portion of the handlebar would contain wiring from the left hand electrode and the chest electrode, an internal connector would be required to connect these wires to the wiring from the right hand electrode, should disassembly be desired.

In another embodiment a small central section could be added to facilitate elongation so that different sizes of individuals can be easily accommodated. In yet another embodiment, the connector 560 could act as the joining piece. In such an embodiment, the connector 560 would include apertures at opposite ends wherein each handlebar section can be attached. Other variations can be envisioned within the spirit and scope of the invention.

Figure 6:
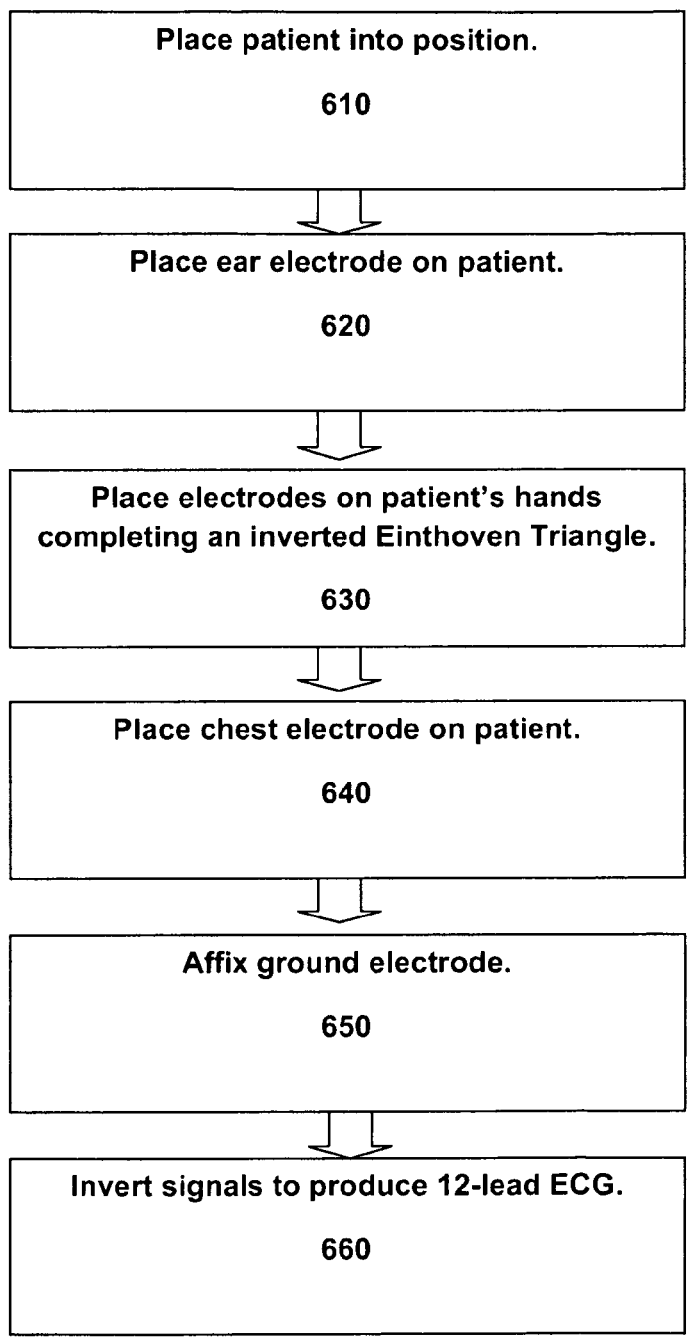
FIG. 6 shows a flow chart of a method for producing a 12-lead ECG without a leg electrode, according to an embodiment of the present invention.

Referring to FIG. 6, there is shown a flow chart 600 of a method according to an embodiment of the present invention. First, in step 610, the patient is placed into position. In a hospital setting, the patient generally is placed supine on a table. For this method, it is not necessary to have the patient recumbent. The patient may stand or sit while the procedure takes place.

Next in step 620, electrode 220 is placed on the patient, in or on one of the patient's ears. It is also possible to place one electrode in or on each ear. In step 630 two electrodes 210 and 215 are placed in each of the patient's hands. Now the inverted Einthoven triangle is complete.

In step 640 an electrode 310 is placed in the chest area of the patient. Next, an electrode acting as ground is attached to the patient's contralateral ear 225 in step 650. Lastly, in step 660, the signals from the receiving electrodes are inverted to produce a conventional 12-lead electrocardiogram recording.

Figure 7:
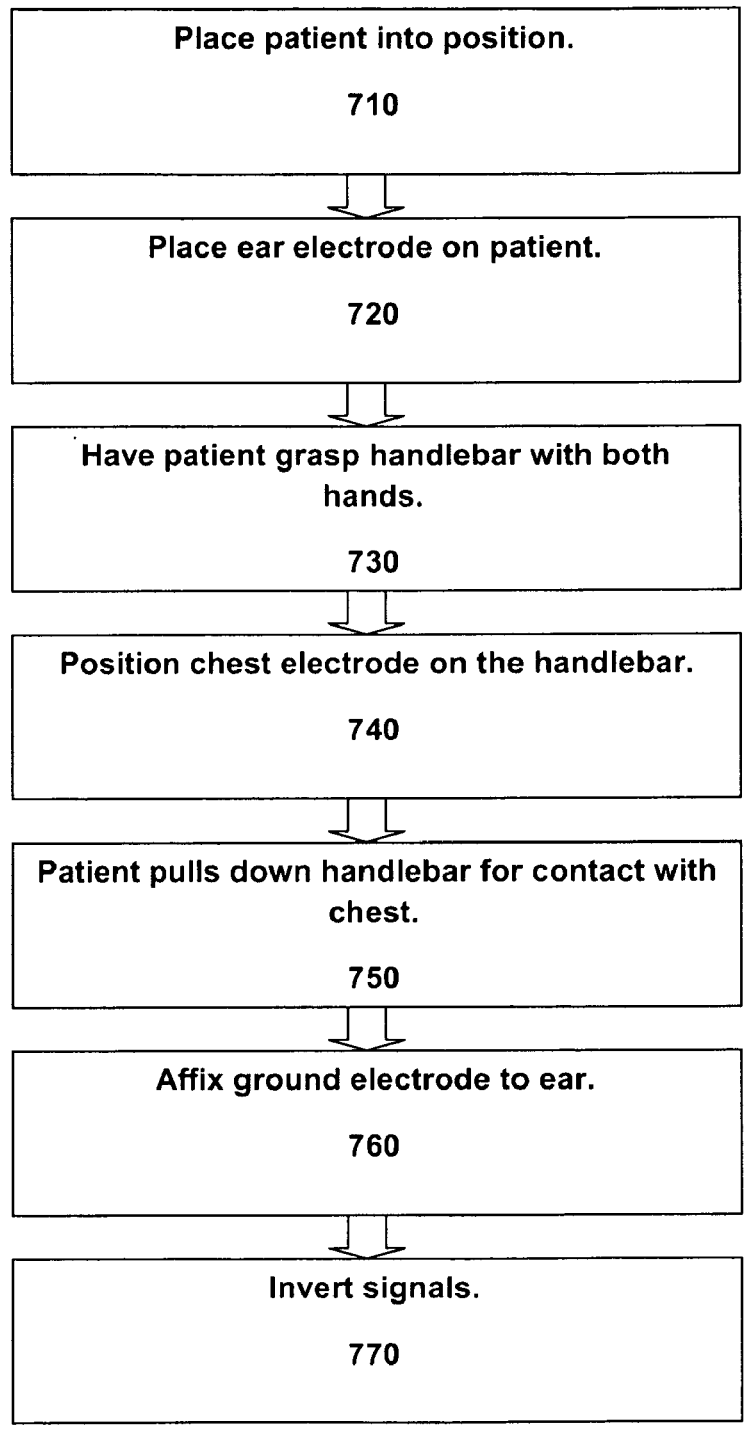
FIG. 7 shows a flow chart of a handlebar method for producing a 12-lead ECG without a leg electrode, according to an embodiment of the present invention.

Referring to FIG. 7 there is shown a flow chart 700 of a method according to another embodiment of the present invention. First, in step 710, the patient is placed into position. Again, for this method, it is not necessary to have the patient recumbent. The patient may stand or sit while the procedure takes place.

Next in step 720, electrode 220 is placed on the patient, in or on the patient's ears. In step 730 the patient grasps the ends of the handlebar 550 with both hands, thus making contact with the end electrodes of the handlebar 550. The patient does not need to squeeze the handlebar; it is sufficient to grasp firmly so that the palm of the hand and the fingers are in substantial contact with the handlebar end. When the patient grasps the handlebar and makes contact with the end electrodes the inverted Einthoven triangle is complete.

Next in step 740 the chest electrode 510 on the handlebar 550 is positioned to the desired location over the patient's chest. The patient next pulls down the handlebar 550 so that the center chest electrode 510 is in contact with the patient's chest in step 750. Note that is preferable to position the chest electrode 510 slightly to the left of the sternum. The position of the chest electrode 510 may need to be adjusted after the handlebar 550 is placed on the chest.

Next, an electrode acting as ground is attached to the patient's contralateral ear 225 in step 760. Lastly, in step 770, the signals from the receiving electrodes are inverted to produce a conventional 12-lead electrocardiogram recording.

Figure 9:
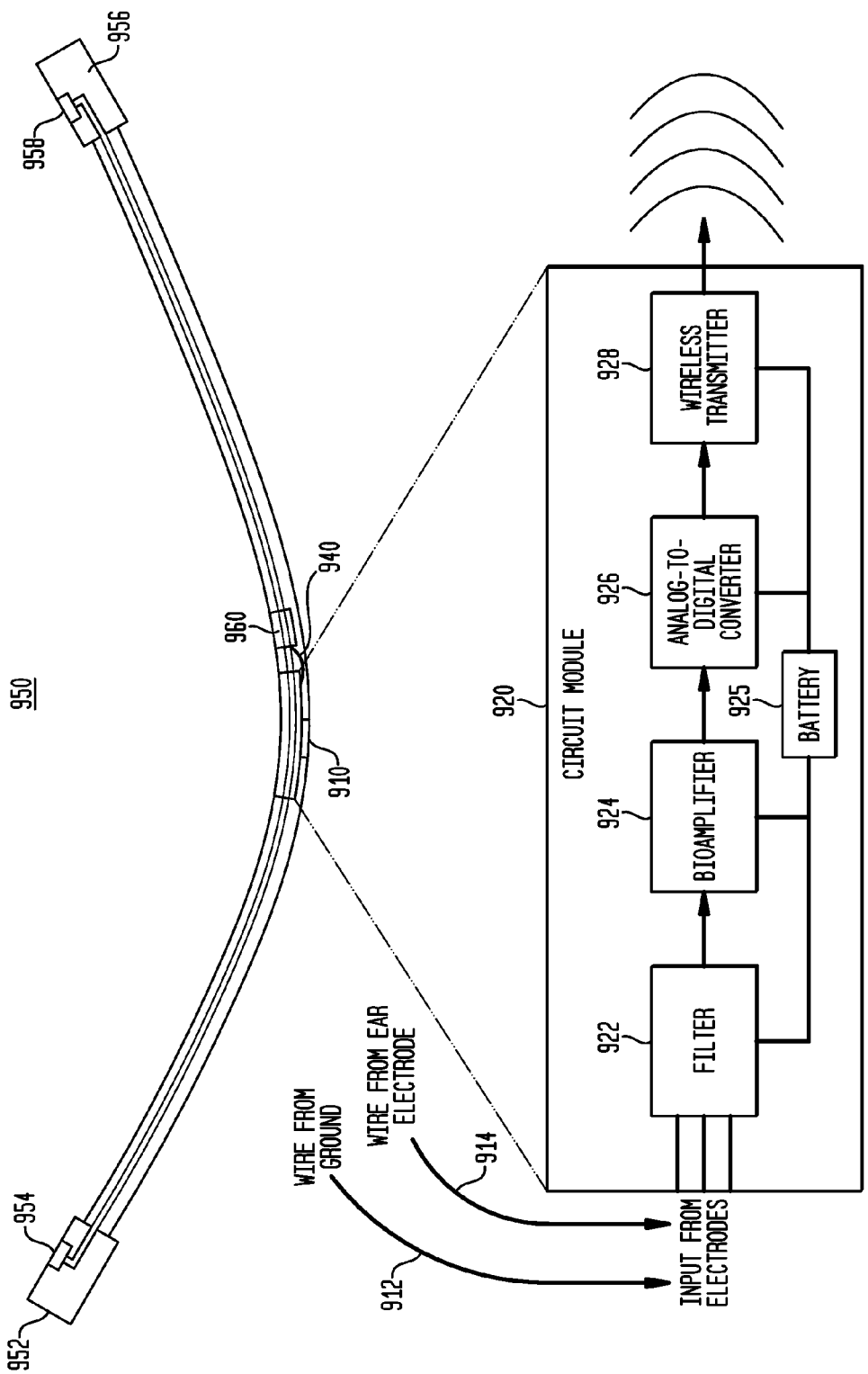
FIG. 9 shows a wireless handlebar apparatus, according to an embodiment of the present invention.

With reference now to FIG. 9 there is shown a wireless handlebar apparatus 950 according to another embodiment of the present invention. The wireless handlebar 950 is substantially similar to the handlebar apparatus 550 of FIG. 5A, except that the wireless embodiment includes a circuit module 920 for transmitting signals to a computer or display device. A further difference is that the wireless embodiment 950 does not require the efferent cable 562 as shown in FIG. 5A.

The wireless handlebar apparatus 950 can be embodied in the same form factors as the wired embodiment 550. The example shown here in FIG. 9 is a gentle u-shaped form factor. The patient grasps the upright ends 952 and 956 of the handlebar 950. The handlebar 950 is aligned over the patient along the plane of the nipples. The center chest electrode 910 is positioned slightly to the left of the sternum. This chest electrode 910 is able to "slide" along the center portion of the handlebar 950 a few inches in each direction to give some versatility to the chest and hand positions. Just like with the wired version, the patient grasps the ends of the handlebar 950 and places the handlebar 950 on his/her chest, making contact with the skin at the point of the chest electrode 910.

To secure accurate readings, a fourth electrode 220 (not shown here) is affixed to the patient's ear, forming the apex of the inverted Einthoven triangle. Lead wire 914 from this ear electrode 220 is input into the circuit module 920. An additional lead wire 912 from ground is also input into the circuit module 920.

In one possible embodiment, the right 956 and left 952 ends of the handlebar 950 are fixed contact surfaces which function as electrodes 954 and 958 and encircle the handlebar 950. The handles 952 and 956 are circumferential. The electrodes 954 and 958 make contact with the patient's hands and are connected by internal wires to the connector 960 near the center of the handlebar 950. The connector 960 is in turn electronically coupled with the circuit module 920 by a cable 940.

The circuit module 920 receives the lead wire signals, converts them, and then transmits the converted signals wirelessly to a computer (not shown) or display screen. The components of the circuit module 920 are:

a filter 922 for receiving the lead wires 912 and 914 as input;

a bioamplifier 924 for amplifying the signals from the filter 922;

an analog-to-digital converter 926 for converting the signals from the bioamplifier 924;

a wireless transmitter 928 for transmitting the signals to the computer or other device; and a battery 925 operatively coupled with the above components for providing power to the components.

Therefore, while there have been described what are presently considered to be the preferred embodiments, it will be understood by those skilled in the art that other modifications can be made within the spirit of the invention.

The invention claimed is:

1. A method for measuring cardiac electrical activity of a patient, the method comprising steps of:
    forming an inverted Einthoven triangle of electrocardiograph electrodes for placement on the patient, the step of forming comprising steps of:
    attaching a first receiving electrode to an ear of the patient, the first electrode forming an apex of the inverted Einthoven triangle;
    and attaching second and third receiving electrodes to each of the patient's arms, forming a base of the inverted Einthoven triangle;
    attaching a fourth electrode to a chest area of the patient;
    wherein the receiving electrodes are coupled with a connector by lead wires and wherein the connector is operatively coupled to a processor;
    wherein an electrical ground electrode is further coupled to the connector by another lead wire; and
    electronically inverting signals obtained from the first, second, third, and fourth electrodes to produce vectors enabling a calculation of a conventional twelve lead electrocardiogram recording using the processor.

2. The method of claim 1, further comprising attaching the electrical ground electrode to a contralateral ear of the patient.

3. The method of claim 1 wherein the second receiving electrode is attached to the patient's right arm such that a pairing of the right arm and the ear act as an inverted lead II; and
    wherein the third receiving electrode is attached to the patient's left arm such that a pairing of the left arm and the ear act as an inverted lead III; and
    wherein a pairing of the right arm and the left arm act as lead I.

4. The method of claim 3 wherein electronically inverting signals further comprises:
    mathematically transforming readings taken from leads II and III back to a conventional Einthoven configuration by taking into account: an angular variation of a cardiac dipole measured by the ear electrode as opposed to a left leg electrode; and
    a magnitude variation of the cardiac dipole measured by the ear electrode as opposed to a left leg electrode.

5. The method of claim 1 wherein the electrical ground electrode is affixed to the patient.

6. A method for measuring cardiac electrical activity of a patient, the method comprising:
    forming an inverted Einthoven triangle of electrocardiograph electrodes for use on the patient, the step of forming comprising steps of:
    attaching a first receiving electrode to an ear of the patient, said first receiving electrode forming an apex of the inverted Einthoven triangle;
    and placing a non-linear shaped tube in an upright position above the patient's chest, wherein the tube comprises:
    a center portion between right and left upright ends of the tubular structure;
    a second receiving electrode in the left upright end;
    a third receiving electrode in the right upright end;
    a fourth receiving chest electrode positioned in a center portion of the tube;
    a connector operatively coupled with a processor;
    internal electrical lead wires for joining the electrodes with the connector;
    an efferent cable for coupling the connector with the processor;
    having the patient grasp each upright end of the tube, forming a base of the inverted Einthoven triangle;
    positioning the fourth receiving electrode in the center portion of the tube above the patient's chest;
    having the patient pull down and hold the tube in place such that the fourth electrode makes contact with the patient's skin in the chest area, and such that no other part of the tube makes contact with the patient's chest area;
    affixing an electrical ground electrode to a ground surface, wherein said electric ground electrode is coupled to the connector by a lead wire;
    and electronically inverting signals obtained from the first, second, third, and fourth electrodes to produce vectors enabling a calculation of a conventional twelve lead electrocardiogram recording using the processor.

7. The method of claim 6 wherein the step of positioning the fourth electrode comprises an initial step of:
    sliding the fourth electrode along the tube until a desirable position is found in the patient's chest area.

8. The method of claim 7 wherein the desirable position is slightly left of a sternum of the patient.

9. An apparatus for measuring cardiac electric activity of a patient, said apparatus comprising:
    a tubular structure embodied in a lightweight, non-linear form factor, wherein the tubular structure comprises:
    a center portion between right and left upright ends of the tubular structure; a connector positioned in the center portion;
    a first receiving electrode in the left upright end;
    a second receiving electrode in the right upright end;
    a third receiving electrode in the center portion for placement on a chest of the patient in an area of a cardiac silhouette, such that only said third receiving electrode makes contact with the patient's chest;

internal electrical lead wires for joining the receiving electrodes to the connector;

an efferent cable for coupling the connector with a processor for electronically inverting signals obtained from the electrodes to produce vectors enabling a calculation of a conventional twelve lead electrocardiogram recording using the processor, wherein the processor is operatively coupled with a fourth electrode affixed to an ear of the patient.

10. The apparatus of claim 9 wherein the tubular structure is formed of a lightweight, thermoplastic, self-insulating material.

11. The apparatus of claim 9 wherein the tubular structure is formed of a metal.

12. The apparatus of claim 11 wherein the internal electrical lead wires and the receiving electrodes are insulated.

13. The apparatus of claim 9 wherein the chest electrode is able to slide along the center portion of the tubular structure.

14. The apparatus of claim 9 wherein the first and second receiving electrodes comprise hollow tubular bars that encircle the upright ends of the tubular structure and comprise fixed contact surfaces.

15. The apparatus of claim 9 wherein the tubular structure is formed of two separate sections that are joined together and then disassembled for storage.

16. The apparatus of claim 15 further comprising a junction part for joining the two separate sections.

17. The apparatus of claim 9 wherein the fourth electrode is operatively coupled with the connector by a lead wire.

18. The apparatus of claim 9 wherein the non-linear form factor comprises a quasi-u shape.

19. An apparatus for measuring cardiac electric activity of a patient, said apparatus comprising:
a tubular structure embodied in a lightweight, non-linear form factor, wherein the tubular structure comprises:
a center portion between right and left upright ends of the tubular structure, said center portion comprising:
a connector for coupling lead wires from receiving electrodes with a circuit module;
the circuit module operatively coupled with the connector for electronically inverting signals obtained from the receiving electrodes to produce vectors enabling a calculation of a conventional twelve lead electrocardiogram recording for display, wherein said circuit module comprises:
a filter for receiving signals from an ear electrode and a ground electrode; a bio-amplifier for amplifying the signals from the filter;
an analog-to-digital converter for converting the amplified signals;
a wireless transmitter for transmitting the converted signals to the display;
and a battery operatively coupled with the filter, the bio-amplifier, the analog-to-digital converter and the wireless transmitter for powering same;
a first receiving electrode in the left upright end of the tubular structure; a second receiving electrode in the right upright end of the tubular structure;
a third receiving electrode in the center portion for placement on a chest of the patient in an area of a cardiac silhouette, such that only said third receiving electrode makes contact with the patient's chest;
and internal electrical lead wires for joining the receiving electrodes to the connector.

20. The apparatus of claim 19 wherein the tubular structure is formed of a lightweight, thermoplastic, self-insulating material.

21. The apparatus of claim 19 wherein the chest electrode is able to slide along the center portion of the tubular structure for optimal positioning.

22. The apparatus of claim 19 wherein the first and second receiving electrodes comprise hollow tubular bars that encircle the upright ends of the tubular structure and comprise fixed contact surfaces.

* * * * *